United States Patent [19]

Hellman, Jr.

[11] Patent Number: 4,828,669

[45] Date of Patent: May 9, 1989

[54] ELECTROPHORESIS DEVICE WITH REMOVABLE BUFFER TANK

[75] Inventor: Robert R. Hellman, Jr., Southbury, Conn.

[73] Assignee: Eastman Kodak Company, Rochester, N.Y.

[21] Appl. No.: 187,152

[22] Filed: Apr. 28, 1988

[51] Int. Cl.⁴ .................. G01N 27/28; G01N 27/26
[52] U.S. Cl. ............................. 204/299 R; 204/182.8
[58] Field of Search ............. 204/182.8, 182.9, 299 R

[56] References Cited

U.S. PATENT DOCUMENTS

| | | | |
|---|---|---|---|
| 3,129,158 | 4/1964 | Raymond et al. | 204/299 R |
| 3,374,166 | 3/1968 | Raymond | 204/299 R |
| 4,305,799 | 12/1981 | Schwartz et al. | 204/299 R |
| 4,715,942 | 12/1987 | Tezuka et al. | 204/182.8 X |
| 4,773,984 | 9/1988 | Flesher et al. | 204/182.8 X |

OTHER PUBLICATIONS

Bio-Rad Price List M, 4/87.

*Primary Examiner*—John F. Niebling
*Assistant Examiner*—John S. Starsiak, Jr.
*Attorney, Agent, or Firm*—Dana M. Schmidt

[57] ABSTRACT

There is disclosed an electrophoresis device comprising a gel plate assembly on a support, and an upper and a lower buffer tank. At least one of such tanks includes means for releasably mounting the at least one tank in liquid contact with the interior of the gel plate assembly and in removable position on the support, the releasable mounting means including a clamp that biases the at least one tank against the support with the gel plate assembly held between the at least one tank and the support.

10 Claims, 7 Drawing Sheets

ELECTROPHORESIS DEVICE WITH REMOVABLE BUFFER TANK

FIELD OF THE INVENTION

This invention relates to an electrophoresis device and the manner in which the buffer tanks and gel plate assembly are mounted on the device.

BACKGROUND OF THE INVENTION

Electrophoresis sequencers have been provided with a gel plate assembly, usually precisely vertically mounted, and a buffer tank at the top and bottom. On the device called the BRL Model S2, manufactured by Bethesda Research Labs, Gaithersburg, MD, the top buffer tank is part of the support against which the gel plate assembly is clamped. The bottom tank, though removable, provides no significant contribution to holding the gel plate assembly in place. As a result, separate clamping elements have to be individually pulled and/or rotated and released to hold the vertically oriented gel plate assembly from tipping over. Such clamping elements are tedious and time-consuming in their use, particularly if more than four per plate assembly are required. The tedium is enhanced by reason of the fact that, until the clamps are properly secured, the gel plate assembly has to be manually held from tipping over.

Still another problem with top buffer tanks that are integral with the support, is that they are difficult to clean. Autoclaving is an effective decontamination step, except that when the buffer tank is part of the entire electrophoresis device, and not removable therefrom, it is not feasible to autoclave the top buffer tank by autoclaving the entire device.

Yet another problem with the conventional vertical electrophoresis devices is that the upper buffer tank, by reason of its fixed location, did not permit gel plate assemblies of varying lengths to be used. Such varying lengths are encountered because some samples require a longer lane for adequate separation. Thus when a different length is needed, one has to obtain an entirely different device, or at the very least, a different plate assembly plus upper buffer tank, rather than use a gel plate assembly of different length on the same device.

Still another problem with conventional electrophoresis devices is that the clamps used to hold the gel plate assembly in place, provide variable amounts of clamping pressure, depending upon how much they wre screwed into place. This leads to, in some cases, insufficient clamping pressure, and to compensate for this, in some cases too much pressure that damages the assembly.

SUMMARY OF THE INVENTION

I have designed an electrophoresis device which avoids the above-noted problems of securing the gel plate assembly. This is achieved by using the buffer tanks as the clamping means for holding the gel plate assembly in place, and/or by using a removable clamping means with predictable clamping action for engaging either of the buffer tanks with the device.

More specifically, there is provided an electrophoresis device for electrophoretically separating charged compounds, the device comprising at least one support for mounting at least one gel plate assembly, a pair of buffer tanks for each gel plate assembly, means for mounting the pair of tanks at opposite ends of the each gel plate assembly, and means for applying a current at the opposite ends of the each plate assembly. In accord with one aspect of the invention, the device is improved in that at least one of the buffer tanks includes means for releasably mounting the at least one tank in liquid contact with the interior of the gel plate assembly and in removable position on the support, the releasable mounting means including a clamp that biases the at least one tank against the support with the gel plate assembly held between the at least one tank and the support by the clamp.

In accord with another aspect of the invention, the gel plate assembly is in a generally vertical orientation, and the device is improved in that the buffer tank at the upper end of the gel plate assembly includes positioning means for automatically locating the upper buffer tank relative to the top of the gel plate assembly, and means for mounting the upper buffer tank on the support at the top of the gel plate assembly, whereby the upper buffer tank is useful with gel plate assemblies of variable length.

Thus, it is an advantageous feature of the invention that either buffer tank is removable for cleaning steps that need not include the entire device.

It is a related advantageous feature that the upper buffer tank can be used with a variety of lengths of gel plate assemblies, thus avoiding the need for a separate device for such length.

It is yet another advantageous feature that the mounting of the buffer tanks automatically produces the clamping action needed to hold the gel plate assembly in position.

It is a related advantageous feature that the clamping of the gel plate assembly requires no determination by the user as to the proper amounts of clamping pressure.

Other advantageous features will become apparent upon reference to the following "Detailed Description", when read in light of the attached drawings.

DESCRIPTION OF THE PREFERRED EMBODIMENTS

This invention is described with respect to a preferred electrophoresis device in which both buffer tanks are removable and are attachable using a predetermined clamping action. It is further described as one in which the buffer tanks preferably clamp by clamping the gel plate assembly between them and the support. In addition, certain aspects of the invention are useful even if only one buffer tank is removable, and/or whether or not the gel plate assembly is held between the tank and the support.

Features of the electrophoresis device also described herein, other than the removable buffer tanks, include subject matter that is separately claimed in the following commonly owned related applications co-filed with this application by me: "Lockable, Rotating Electrophoresis Device" bearing Ser. No. 07/187,117; "Improved Electrophoresis Device With Near-Vertical Gel Plates" bearing Ser. No. 07/187,670; and "Improved Gel Plate Assembly for Electrophoresis" bearing Ser. No. 07/187,668.

Parts described herein as being "vertical", "horizontal", "up", "bottom" or with similar direction terms, refer to their orientation when in their normal use.

Figure 1:
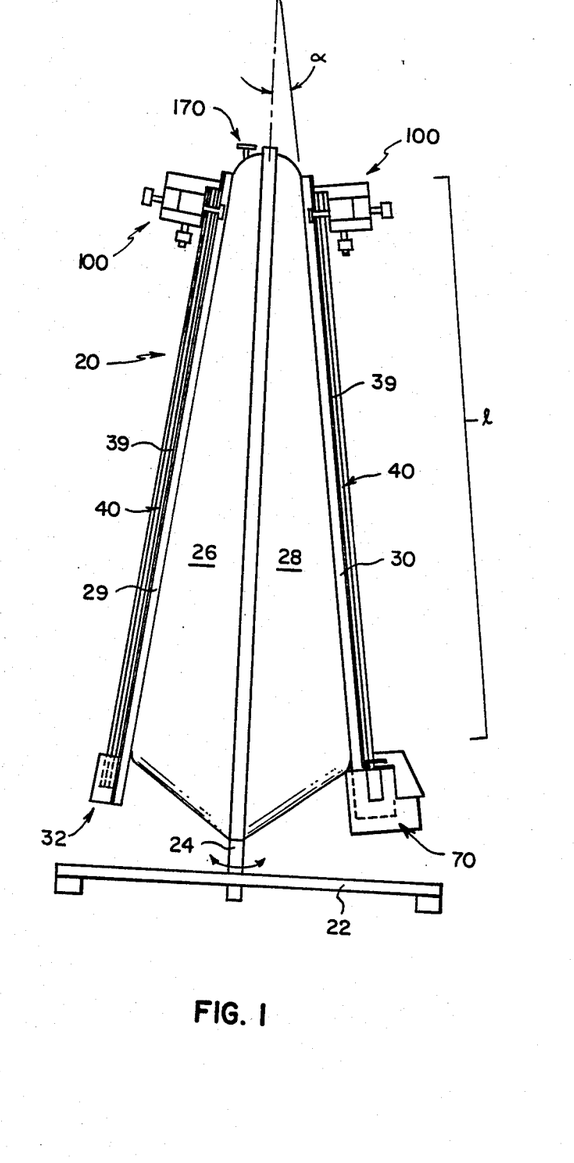
FIG. 1 is an elevational view of an electrophoresis device incorporating the features of the invention.
Figure 2:
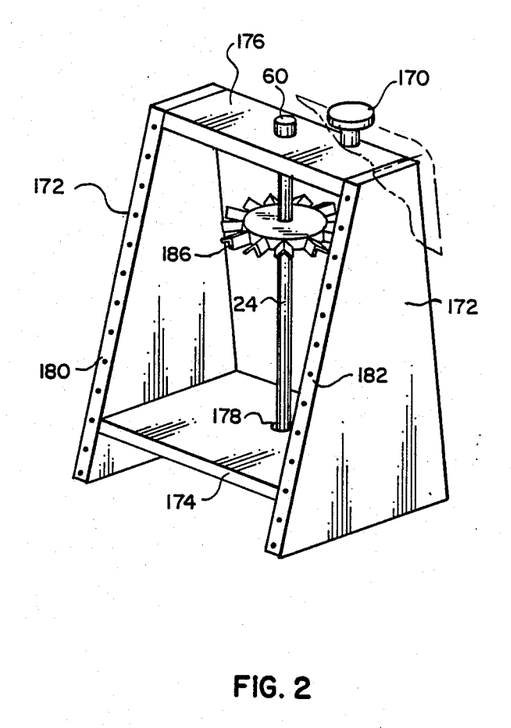
FIG. 2 is a fragmentary isometric view of the interior of the device, partly illustrating the rotatability and lockability of the device.
Figure 3:
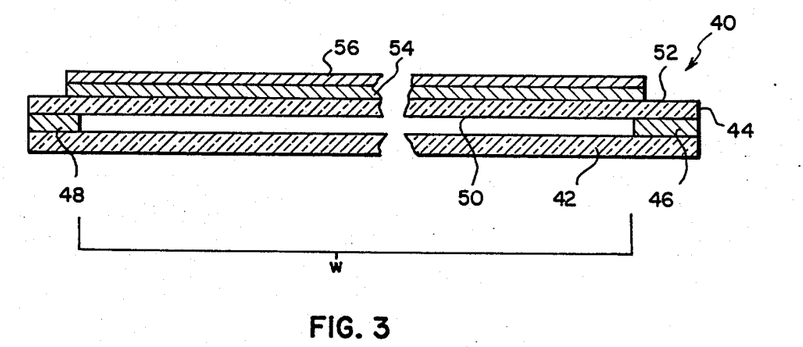
FIG. 3 is a fragmentary sectional view of the gel plate assembly.

An electrophoresis device 20 constructed in accordance with the invention comprises, FIG. 1, a support generally comprising a base 22, a vertical post 24, two clam shell bodies 26, 28 mounted on either side of post 24, and supporting rails 29, 30 providing a support surface for a gel plate 40 that is more completely shown in FIG. 3. Shell bodies 26 and 28 are mounted for rotation, FIG. 2, on post 24, by reason of bushing 60 that rides on the point of post 24. A locking mechanism 170 is provided, effective to releasably hold shells 26, 28 against further rotation. A pair of buffer tanks 70 and 100 are mounted at the bottom of device 20, FIG. 1, and top, respectively, as is conventional. (Only one bottom buffer tank 70 as shown in FIG. 1 for clarity, to allow illustration of trough 32.)

Figure 4:
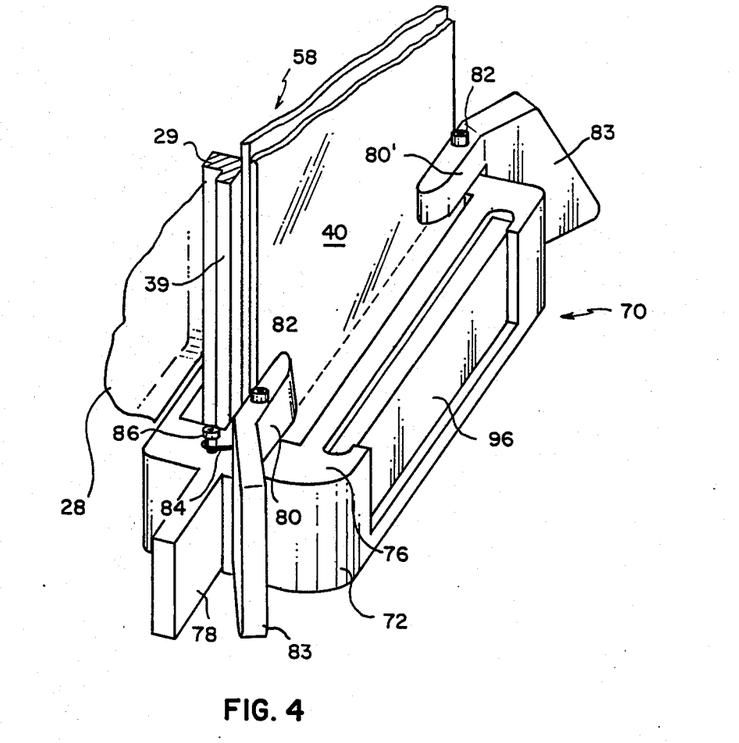
FIG. 4 is a fragmentary isometric view of the bottom buffer tank of the device.
Figure 5:
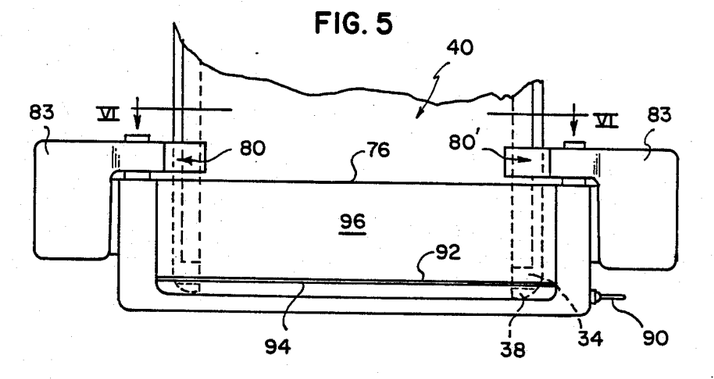
FIG. 5 is a fragmentary front elevational view of the tank of FIG. 4.
Figure 6:
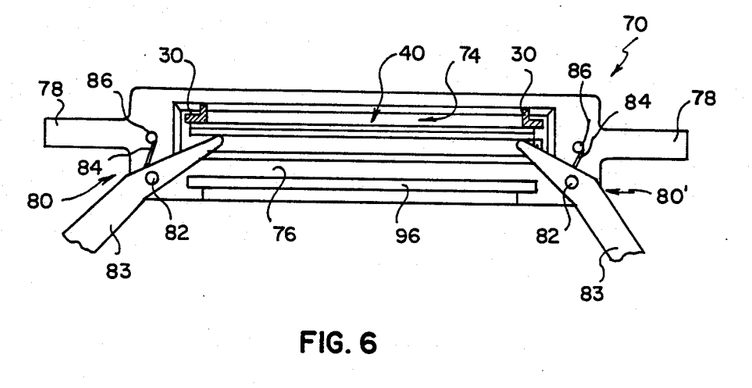
FIG. 6 is a sectional view taken along the line VI—VI of FIG. 5.

Although the supporting surface can be any suitable surface, preferably each of rails 29, 30 is a pair of rails, FIGS. 5 and 6, to provide the supporting surface for gel plate assembly 40. As is seen more clearly in FIGS. 5 and 7, the bottom of each rail features a supporting trough 32 with a front lip 34, that holds gel plate 40 from falling off the rails-see also FIG. 1. Trough 32 in turn comprises a vertical shoulder 36 and a bottom ledge 38. Further, each rail 29, 30 includes a flange 39 that extends the length of the rail, FIGS. 4, 7-8, and 10, to cooperate with clamps for the buffer tanks, as described hereinafter.

Each of the pairs of rails 29 or 30 is associated with its own clam shell. As such, the device permits two electrophoresis gel plate assemblies to be run simultaneously. Alternatively, additional pairs (not shown) can be mounted from the same post, the support being rotated about post 24 until the desired gel plate unit is facing the operator.

Preferably, the gel plate supporting surfaces comprising the pair of rails is mounted to form an angle $\alpha$, FIG. 1, that is inclined from the vertical by an amount between about 5° and 10°. As such, the bottom of the gel plate and buffer tank 70 are closer to the operator, when the gel plate faces the operator, than are the top of the gel plate and buffer tank 100. The advantage is that, unlike perfectly vertical plate supports of conventional devices, no care is required to hold the plate on the support while clamps are mounted in place. Instead, the plate is simply inserted into troughs 32, and leaned back against rails 29 or 30. The trough 32 are effective in preventing the plate from dropping lower, and angle $\alpha$ is effective in preventing plate 40 from tipping over, until buffer tanks 70 and 100 are installed.

Angle $\alpha$ is preferably no less than 5°, since otherwise the angle is insufficiently different from a vertical orientation, and tipping is more likely. It is preferably no greater than 10°, since more than that tends to make the device too bulky at the bottom.

Gel plate assembly 40, FIG. 3, is the entire assembly shown, which comprises a front plate 42, a rear plate 44, and spacers 46, 48 separating the two to allow gel (not shown) to be formed between them, as is conventional. Preferably, rear plate 44 is improved to insure superior formation and observance of dye lines in electrophoresed samples. That is, plate 44 comprises a front surface 50 and a rear surface 52. Rear surface 52 is preferably coated with a mirroring material 54, such as silver or aluminum, and a layer 56 is bonded over coating 54 substantially over the entire area in back of the flow surface area of plate assembly 40. As used herein, the bonding of layer 56 over an area "in back of the flow surface area" of the gel plate means, over an area having an extension that is coincident with, and behind, the flow surface area of the gel, wherein the electrophoresis lanes lie. This area is defined by length "1", FIG. 1, and width "w", FIG. 3. Layer 56 is selected from a material that is effective in distributing or transferring heat, for example, aluminum. This layer is tightly bonded to coating 54 over all of its surface, by using any suitable means, for example an adhesive such as an acrylic adhesive. The entire laminate is then overcoated with a non-conductive layer.

However, layer 56 is *not* used to dissipate heat from the gel plate. Rather, the supporting surfaces formed by rails 39 are deliberately held off from body 28 a distance effective to create a dead air space 58, FIGS. 4 and 8. This insulating air space insures that the heat generated by the process remains in place, thus reducing the time needed to achieve operating temperature.

Layer 56 is thus effective to transfer heat from the hotter center regions, to the peripheral regions, thereby reducing temperature gradients. As a result, dye lines form in the gel that have the desired straightness, and the results are free of thermally induced artifacts. The overall temperature, however, remains high, thus inducing the dye fronts to progress fater than is the case with water-backed units. That is, the water takes much longer to heat up to operating temperature.

The ability of the dye fronts to be processed substantially free of artifacts remains even when supplying as much as 60 watts of power to achieve temperatures as high as 70° C., when measured at the front of plate 42, producing dye front speeds as high as 0.5 cm/min.

Yet another advantage of such a gel plate assembly is the mirrored surface. This surface insures that the user can more readily tell the condition of surface 50, FIG. 3. That is, the mirrored surface makes it easier to accurately introduce sample solution by pipette into the cavity between plates 42 and 44. It also helps reveal particles of dirt, if any, on surface 50 when plate 44 is being cleaned. The dye lines are also more easily detected with the mirror in place.

In accord with one aspect of the invention, one or both, preferably both, of the buffer tanks are removable and hence autoclavible. Most preferably, they are releasably mounted by clamping means that not only clamp the box in position, but also clamp the gel plate to the support.

Figure 7:
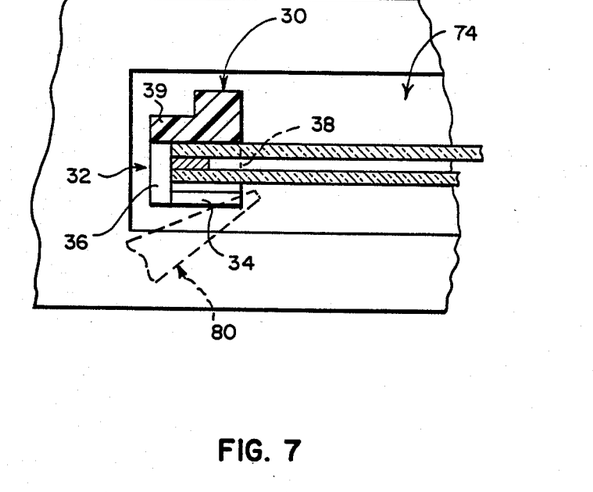
FIG. 7 is a fragmentary enlargement of the portion of FIG. 6 identified as "VII"

With respect to the bottom buffer tank 70, FIG. 4, such tank comprises a cavity 74, FIGS. 6 and 7, open at top surface 76, FIG. 5. The tank has manual grasping ears 78 at either end, and two clamps 80, 80' journalled on post 82 to top surface 76. Each clamp has a handle portion 83. A torsion spring 84 is wrapped around post 82 at one end, FIG. 6, and secured at its other end to a screw 86 attached to surface 76. As a result, clamps 80 and 80' are biased to press inwardly-that is, clamp 80 is biased to rotate counterclockwise, FIG. 6, and 80' to rotate clockwise.

The effect is to not only clamp tank 70 to the support at rails 29, but preferably also to clamp gel plate assembly 40 between the buffer tank and the rails 29. By this construction, it is not necessary that separate clamps or fasteners be used to hold tank 70 in place, apart from those used to clamp the gel plate in place.

Clamps 80 and 80' work by simply grasping the clamp with the thumb and one of the ears with the fingers, and pressing against the torsion spring to release the clamp from contact with the gel plate. This in turn releases the buffer tank from engagement with rails 29 or 30, so that the buffer tank can be removed and cleaned.

As is conventional, a banana plug 90 is mounted at the side of tank 70 for connection to power wires. Inside the tank, plug 90 connects with a wire electrode 92, FIG. 5, that is supported by a rod or tube 94 that extends along the bottom of tank 70. Tube 94 and electrode 92 are preferably removable as a unit.

Preferably, the front face 98 of tank 70 is transparent, to aid in viewing the contents thereof.

Figure 8:
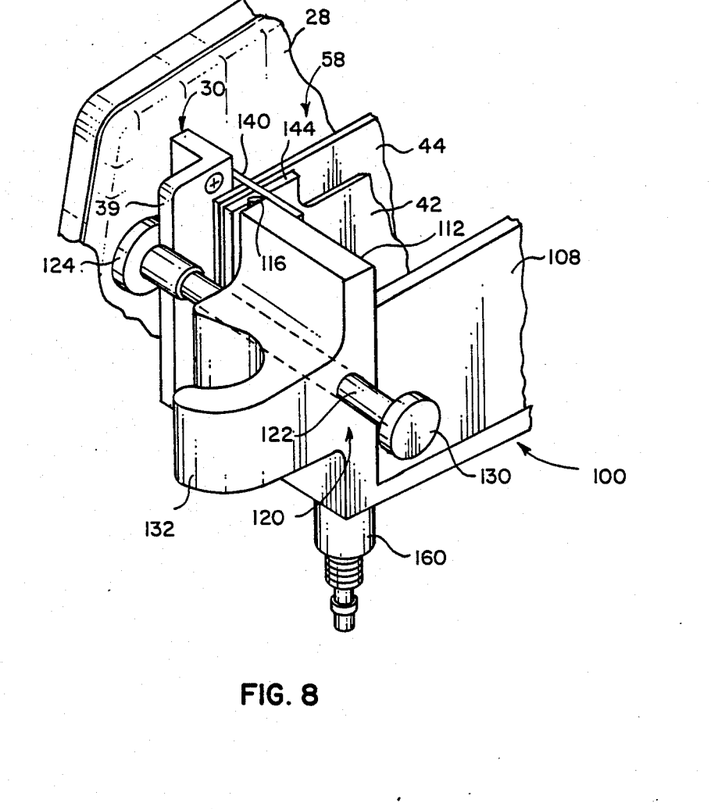
FIG. 8 is a fragmentary isometric view of the upper buffer tank of the invention.
Figure 9:
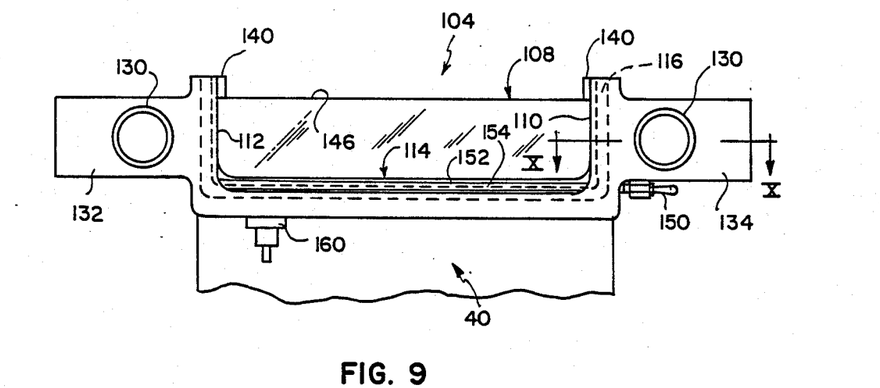
FIG. 9 is a front elevational view of the buffer tank of FIG. 8, as it is placed on a gel plate assembly.
Figure 10:
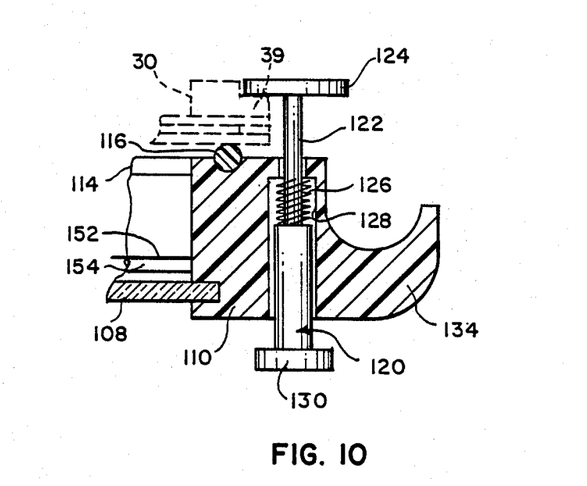
FIG. 10 is a fragmentary sectional view taken generally along the line of X—X of FIG. 9.

Similarly, tank 100 can be releasably clamped to the other end of gel plate assembly 40, FIG. 8-10. Tank 100 also comprises a cavity 104 defined by a bottom surface 106, FIG. 10, a front transparent plate 108, FIGS. 8-10, side walls 110, 112, and a very short vertical back wall 114. Back wall 114 is shorter than the height of front plate 108, so that liquid in cavity 104, FIG. 9, will contact gel plate assembly 40 (shown in phantom, FIG. 10) in contact with the tank 100. To insure the liquid does not pour out of cavity 104, a gasket 116 (shown in phantom in FIG. 9) traces a U-shape in a track along the back of sidewalls 110, 112 and back wall 114, FIGS. 9 and 10.

The clamps for tank 100 comprise a plunger 120, FIGS. 8 and 10, having a shaft 122 that extends through sidewall 110, to a disc 124 dimensioned to engage flange 39. Inside wall 110, shaft 122 is reduced in diameter, FIG. 10, to accommodate a compression spring 126 mounted within aperture 128 for the clamp. Button 130 is used to press the clamp against the bias of spring 126, thereby releasing the clamp, the buffer tank, and gel plate assembly 40 from engagement with rail 29 or 30. Gripping ears 132, 134, FIGS. 8-10, are provided to assist in manually depressing plunger 120 and thus overcoming the bias of spring 126.

Any compression spring is useful for spring 126. Preferably, it is one providing a spring constant of about 0.735 N/mm, such as is achieved by two end-to-end springs P/N CO 480-045-2000 S manufactured by Associated Spring, Bristol, CT.

Other clamps can be used in place of the plungers 120. For example, pivoting clamps like those of bottom buffer tank 70, FIG. 4, could be mounted and biased to pivot about a vertical axis towards the back-side of rail 39. Similarly, the clamps of bottom buffer 70 could be replaced with the plungers 120 of the upper buffer tank, biased to press against gel plate assembly 40. Release in both cases would occur by pulling on the clamp mechanism. Because pushing is considered to be easier, the clamp arrangement actually shown is preferred.

Such clamps as described above have the advantage of applying substantially the same predetermined pressure against the gel plate assembly, thus avoiding the need to estimate the amount of clamping pressure each time the plate assembly is mounted.

A further improvement in tank 100 is the use of means that automatically position the tank at the top of gel plate 40. These comprise locators 140 that extend generally flush with top surface 142 of cavity 104, back beyond gasket 116. Locators 140 are essentially ears, constructed to ride on the top 144 of gel plate assembly 40, FIG. 8 (which top coincidentally coincides with the top surface 146 of front plate 108, FIG. 9). Because locators 140 fit between the paired rails, FIG. 8, they also serve to locate tank 100 sideways on the assembly 40.

By reason of this construction, any length gel plate can be used in the device, without preventing tank 100 from being at the top of the assembly, provided the length is not greater than the length of rails 29 or 30. That is, tank 100 will always be located at the top of gel plate 40, since locators 140 insure this.

Banana plug 150, wire 152 and supporting rod 154 are mounted in tank 100, FIGS. 9 and 10, in a manner similar to that of lower tank 70.

As is conventional, a drain valve 160 is mounted in bottom surface 106, FIGS. 8 and 9, for draining the tank.

Alternatively, not shown, plate 108 can be a magnifying plate to provide magnification.

The frame by which device 20 rotates comprises, FIG. 2, trapezoids 172 mounted vertically on two horizontal plates 174 and 176. Plate 174 is apertured at 178 to allow post 24 to freely extend through it. Plate 176 provides bushing 60, described hereafter. The outwardly facing edges 180, 182 of each trapezoid 172 provide the mounting support for the pairs of rails mounting on the clam shell bodies, shown in phantom. Bushing 60, FIG. 11, rides on point 184 of post 24. In this fashion, the entire frame comprising plate 174, 176, bushing 60, trapezoids 172 and the attached clam shell bodies and rails, rotates on post 24.

Preferably rotation of the device is temporarily interrupted by the locking mechanism 170, FIG. 2. Mechanism 170 features a two-position push latch, of a conventional construction, not shown, effective to cause a member to engage or disengage the teeth of a lock plate 186.

The invention has been described in detail with particular reference to preferred embodiments thereof, but it will be understood that variations and modifications can be effected within the spirit and scope of the invention.

What is claimed is:

1. In an electrophoresis device for electrophoretically separating charged compounds, the device comprising at least one support for mounting at least one gel plate assembly, a pair of buffer tanks for each gel plate assembly, means for mounting said pair of tanks at opposite ends of said each gel plate assembly, and means for applying a current at said opposite ends of said each plate assembly;

the improvement wherein at least one of said buffer tanks includes means for releasably mounting said at least one tank in liquid contact with the interior of said gel plate assembly and in removble position on said support, said releasable mounting means including a clamp that biases said at least one tank against said support with said gel plate assembly held between said at least one tank and said support by said clamp.

2. A device as defined in claim 1, wherein both of said tanks include said mounting means so that said gel plate assembly is held in position on said support by a clamp of said respective buffer tank.

3. In an electrophoresis device for electrophoretically separating charged compounds, the device comprising at least one support for mounting at least one gel plate assembly in a generally vertical orientation, a pair of buffer tanks for each gel plate assembly, means for mounting said pair of tanks at opposite ends of said each gel plate assembly, and means for applying a current at said opposite ends of said each plate assembly;

the improvement wherein said buffer tank at the upper end of said gel plate assembly includes positioning means for automatically locating said upper buffer tank relative to the top of said gel plate assembly, and means for mounting said upper buffer tank on said support at said top of said gel plate assembly, whereby said upper buffer tank is useful with gel plate assemblies of variable length.

4. A device as defined in claim 3, wherein said mounting means for said upper buffer tank comprise releasable mounting means, whereby said upper tank is readily removed from said support.

5. A device as defined in claim 4, wherein said support for said gel pate assembly includes a pair of rails at either side of said gel plate assembly, each rail comprising a front surface and a back surface, said front surface being constructed to contact a gel plate assembly, and said releasable mounting means comprise a) a clamp at each side of said upper buffer tank, positioned to press against said rail back surfaces, b) means for biasing said clamp against said rail back surface with said gel plate assembly between said rails and said upper buffer tank, and c) means for manually overcoming said biasing means.

6. In an electrophoresis device for electrophoretically separating charged compounds, the device comprising at least one support for mounting at least one gel plate assembly in a generally vertical orientation, a pair of buffer tanks for each gel plate assembly, means for mounting said pair of tanks at opposite ends of said each gel plate assembly, and means for applying a current at said opposite ends of said each plate assembly;

the improvement wherein said buffer tank at the top of said gel plate assembly further includes means for releasably mounting said top buffer tank in a removable position on said support, with a gel plate assembly held between said upper buffer tank and said support.

7. A device as defined in claim 6, wherein said support for said gel plate assembly includes a pair of rails at either side of said gel plate assembly, each rail comprising a front surface and a back surface, said front surface being constructed to contact a gel plate assembly, and said releasable mounting means comprise (a) a clamp at each side of said upper buffer tank, positioned to press against said rail back surfaces, (b) means for biasing said clamp against said rail back surface with said gel plate assembly between said rails and said upper buffer tank, and (c) means for moving said clamp away from said rail against the force of said biasing means.

8. In an electrophoresis device for electrophoretically separating charged compounds, the device comprising at least one support for mounting at least one gel plate assembly in a generally vertical orientation, a pair of buffer tanks for each gel plate assembly, means for mounting said pair of tanks at opposite ends of said each gel plate assembly, and means for applying a current at said opposite ends of said each plate assembly;

the improvement wherein said buffer tank at the bottom of said gel plate assembly includes means for removable clamping said bottom buffer tank to said gel plate assembly and to said support.

9. A device as defined in claim 8, wherein said bottom buffer tank includes a cavity open at the top, configured to receive said gel plate assembly and appropriate liquid, and said clamping means comprise (a) a lever for pressing on said gel plate assembly, said cavity and lever being configured to press said gel plate assembly against said support, and (b) means for biasing said lever against said gel plate assembly.

10. A device as defined in claim 9, and further including (c) grasping means for manually overcoming said biasing means, whereby said bottom buffer tank is removable.

* * * * *